United States Patent
Tsouderos

(10) Patent No.: US 7,544,710 B2
(45) Date of Patent: Jun. 9, 2009

(54) USE OF THE DISTRONTIUM SALT OF 2-[N,N-DI(CARBOXYMETHYL)AMINO]-3-CYANO-4-CARBOXYMETHYL-THIOPHENE-5-CARBOXYLIC ACID FOR THE PRODUCTION OF MEDICAMENTS FOR THE TREATMENT OF GASTRO-DUODENAL PAIN

(75) Inventor: Yannis Tsouderos, Paris (FR)

(73) Assignee: Les Laboratoires Servier, Suresnes Cedex (FR)

( * ) Notice: Subject to any disclaimer, the term of this patent is extended or adjusted under 35 U.S.C. 154(b) by 555 days.

(21) Appl. No.: 10/533,787

(22) PCT Filed: Nov. 4, 2003

(86) PCT No.: PCT/FR03/03279

§ 371 (c)(1),
(2), (4) Date: May 4, 2005

(87) PCT Pub. No.: WO2004/043455

PCT Pub. Date: May 27, 2004

(65) Prior Publication Data

US 2006/0014824 A1    Jan. 19, 2006

(30) Foreign Application Priority Data

Nov. 5, 2002    (FR)    .................................... 02 13805

(51) Int. Cl.
A61K 31/38    (2006.01)
A61K 31/381    (2006.01)

(52) U.S. Cl. ........................ 514/448; 514/447; 514/925; 514/926; 514/927

(58) Field of Classification Search ................. 514/447, 514/448, 925, 926, 927
See application file for complete search history.

(56) References Cited

U.S. PATENT DOCUMENTS

| | | | |
|---|---|---|---|
| 5,128,367 A * | 7/1992 | Wierzbicki et al. | ......... 514/447 |
| 5,856,356 A | 1/1999 | Tsouderos et al. | |
| 5,866,168 A * | 2/1999 | DeLacharriere et al. | ..... 424/639 |
| 6,146,636 A | 11/2000 | Breton et al. | |
| 2002/0055535 A1 | 5/2002 | Leung | |

OTHER PUBLICATIONS

*International Search Report for PCT FR2003/003279*, Feb. 25, 2004.
*International Preliminary Examination Report for PCT FR2003/003279*, May 19, 2004.

* cited by examiner

*Primary Examiner*—Ardin Marschel
*Assistant Examiner*—Donna Jagoe
(74) *Attorney, Agent, or Firm*—Hueschen and Sage

(57) ABSTRACT

The present invention relates to the use of the distrontium salt of 2-[N,N-di(carboxymethyl)amino]-3-cyano-4-carboxymethyl-thiophene-5-carboxylic acid in obtaining medicaments intended for the treatment of gastro-duodenal pain.

3 Claims, No Drawings

USE OF THE DISTRONTIUM SALT OF 2-[N,N-DI(CARBOXYMETHYL)AMINO]-3-CYANO-4-CARBOXYMETHYL-THIOPHENE-5-CARBOXYLIC ACID FOR THE PRODUCTION OF MEDICAMENTS FOR THE TREATMENT OF GASTRO-DUODENAL PAIN

The present invention relates to use of the distrontium salt of 2-[N,N-di(carboxymethyl)amino]-3-cyano-4-carboxymethyl-thiophene-5-carboxylic acid in obtaining medicaments intended for the treatment of gastro-duodenal pain.

The distrontium salt of 2-[N,N-di(carboxymethyl)amino]-3-cyano-4-carboxymethyl-thiophene-5-carboxylic acid has been described in patent specification EP 0 415 850. Its anti-osteoporotic properties allow it to be used in bone diseases such as osteoporosis. It may also be used in the treatment of cutaneous and vascular ageing, liver disorders and dental disorders.

The distrontium salt of 2-[N,N-di(carboxymethyl)amino]-3-cyano-4-carboxymethyl-thiophene-5-carboxylic acid moreover has anti-arthrosic properties making it useful in the treatment of arthrosis as described in patent specification EP 0 813 869.

The Applicant has now discovered that the distrontium salt of 2-[N,N-di(carboxymethyl)amino]-3-cyano-4-carboxymethyl-thiophene-5-carboxylic acid of formula (I) and hydrates thereof have gastro-protective properties allowing their use in obtaining medicaments intended for the treatment of gastro-duodenal pain:

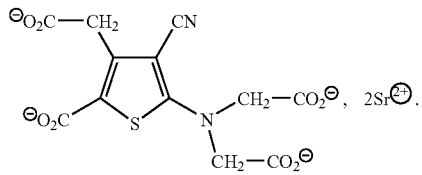

Indeed, it has been shown in a clinical study that the compound of formula (I), which is also referred to as strontium ranelate, was able to bring about a significant improvement in gastric pain.

This result is all the more surprising in that, during an in vivo study carried out with a different strontium salt (strontium chloride), it was observed that strontium chloride very rapidly caused superficial haemorrhagic lesions in the animals treated.

The person skilled in the art would doubtless not have imagined that a different strontium salt, in this case strontium ranelate, would allow the reverse effect to be obtained.

These entirely surprising results accordingly make it possible to consider using strontium ranelate and hydrates thereof in obtaining pharmaceutical compositions for use in the treatment of gastro-duodenal pain and especially gastritis and duodenitis and any inflammation of the mucosa of the stomach whether acute or chronic.

Gastritis and duodenitis correspond to irritative states of the digestive mucosa which are accompanied by daily abdominal pain in rhythm with meals. They are aggravated by different types of food or alcoholic drinks. They may precede the onset of ulcers. They justify the administration of various treatments in order to protect the mucosa or to reduce acid secretion.

The pharmaceutical compositions will be presented in forms suitable for administration by the oral, parenteral, transcutaneous, nasal, rectal or perlingual route, especially in the form of injectable preparations, tablets, sublingual tablets, glossettes, gelatin capsules, capsules, lozenges, suppositories, creams, ointments, dermal gels, etc.

In addition to strontium ranelate or, where appropriate, hydrates thereof, the pharmaceutical compositions according to the invention comprise one or more excipients or vehicles selected from diluents, lubricants, binders, disintegrating agents, absorbents, colourants, sweeteners, etc.

By way of non-limiting example, there may be mentioned:
- as diluents: lactose, dextrose, sucrose, mannitol, sorbitol, cellulose, glycerol,
- as lubricants: silica, talc, stearic acid and its magnesium and calcium salts, polyethylene glycol,
- as binders: aluminium silicate, magnesium silicate, starch, gelatin, tragacanth, methylcellulose, sodium carboxymethylcellulose and polyvinylpyrrolidone,
- as disintegrating agents: agar, alginic acid and its sodium salt, effervescent mixtures.

The useful dosage varies according to the sex, age and weight of the patient, the administration route, the nature of the disorder and any associated treatments, and ranges from 25 mg to 6 g of strontium ranelate per 24 hours, for example from 100 mg to 4 g of compound per 24 hours.

The daily dose of strontium ranelate will preferably be 2 g per day.

Clinical Study:

This study was carried out in 1649 patients. 719 were treated with strontium ranelate, 723 were treated with a placebo. The duration of treatment was 1101±321 days. The dose of strontium ranelate administered was 2 g/day.

After treatment it was observed that gastric pain was significantly reduced in the group of patients treated with strontium ranelate (at least 30%) compared to the group of patients treated with placebo.

The invention claimed is:

1. A method for treating a patient afflicted with gastro-duodenal pain, comprising administration to the patient the distrontium salt of 2-[N,N-di(carboxymethyl)amino]-3-cyano-4-carboxymethyl-thiophene-5-carboxylic acid or hydrates thereof in an amount which is effective for alleviation and treatment of the gastro-duodenal pain.

2. The method of claim 1, wherein the gastro-duodenal pain is pain associated with gastritis.

3. The method of claim 1, wherein the gastro-duodenal pain is pain associated with duodenitis.

* * * * *

UNITED STATES PATENT AND TRADEMARK OFFICE
CERTIFICATE OF CORRECTION

PATENT NO.       : 7,544,710 B2                                          Page 1 of 1
APPLICATION NO.  : 10/533787
DATED            : June 9, 2009
INVENTOR(S)      : Yannis Tsouderos It is certified that error appears in the above-identified patent and that said Letters Patent is hereby corrected as shown below:

Title Page, Item (56) Other Publications: The following cited reference is missing from the Letters Patent "FISCH, et al., Basic and Clinical Pharmaceology and Texicology, 2006, Vol. 98, Pg. 442-446."

Signed and Sealed this

Thirtieth Day of March, 2010

David J. Kappos
*Director of the United States Patent and Trademark Office*